US010736947B2

(12) United States Patent
Dimier-Poisson et al.

(10) Patent No.: US 10,736,947 B2
(45) Date of Patent: Aug. 11, 2020

(54) ***NEOSPORA* FOR USE IN TREATING CANCER AND INFECTIOUS DISEASES**

(71) Applicants: UNIVERSITÉ DE TOURS, Tours (FR); KYMERIS THERAPEUTICS INC., Toronto, Ontario (CA); Institut national de recherche pour l' agriculture, l' alimentation et l'environneement, Paris (FR)

(72) Inventors: Isabelle Dimier-Poisson, Tours (FR); Marie-Noëlle Mevelec, Tours (FR); Céline Ducournau, Louans (FR); Nathalie Moire, Saint-Avertin (FR); Richard McCrae, Hamilton (CA)

(73) Assignees: UNIVERSITÉ DE TOURS, Tours (FR); KYMERIS THERAPUETICS INC., Toronto (CA); Institut national de recherche pour l' agriculture, l' alimentation et l'environneement, Paris (FR)

(*) Notice: Subject to any disclaimer, the term of this patent is extended or adjusted under 35 U.S.C. 154(b) by 0 days.

(21) Appl. No.: 16/003,936

(22) Filed: Jun. 8, 2018

(65) Prior Publication Data

US 2018/0353580 A1 Dec. 13, 2018

(30) Foreign Application Priority Data

Jun. 9, 2017 (EP) .................................... 17305700

(51) Int. Cl.

*A61K 39/00* (2006.01)
*A61K 35/68* (2006.01)
*A61P 35/00* (2006.01)

(52) U.S. Cl.

CPC .......... *A61K 39/0003* (2013.01); *A61K 35/68* (2013.01); *A61K 2039/585* (2013.01); *A61P 35/00* (2018.01)

(58) Field of Classification Search

None

See application file for complete search history.

(56) References Cited

U.S. PATENT DOCUMENTS

2016/0166662 A1 6/2016 Gnahoui-David et al.

OTHER PUBLICATIONS

Dubey et al. 2007 (Epidemiology and Control of Neosporosis and Neospora caninum; Clinical Microbiology Reviews, vol. 20, No. 2, p. 323-367) (Year: 2007).*

Lindsay et al. 1990 (Infections in mice with tachyzoites and bradyzoites of Neospora caninum (Protozoa: Apicomplexa); J Parasitology 76(3):410-413). (Year: 1990).*

Devereux et al. "A comprehensive set of sequence analysis programs for the VAX", Nucleic Acids Research, 1984, pp. 387-395, vol. 12, No. 1.

Altschul et al., "Basic local alignment search tool", Journal of Molecular Biology, 1990, pp. 403-410, vol. 215, No. 3.

Boysen P et al. "The protozoan Neospora caninum directly triggers bovine NK cells to produce gamma interferon and to kill infected fibroblasts," Infectection and Immunity Feb. 2006;74(2):953-60.

Williams DJ et al., "Neospora caninum-associated abortion in cattle: the time of experimentally-induced parasitaemia during gestation determines foetal survival," Parasitology. Oct. 2000;121 ( Pt 4):347-58.

Baird JR et al.,"Avirulent Toxoplasma gondii generates therapeutic antitumor immunity by reversing immunosuppression in the ovarian cancer microenvironment," Cancer Res. Jul. 1, 2013;73(13):3842-51.

Sanders KL et al., "Attenuated Toxoplasma gondii Stimulates Immunity to Pancreatic Cancer by Manipulation of Myeloid Cell Populations," Cancer Immunol Res. Aug. 2015;3(8):891-901.

Rankin EB et al., "An essential role of Th1 responses and interferon gamma in infection-mediated suppression of neoplastic growth," Cancer Biol Ther. Nov.-Dec. 2003;2(6):687-93.

Mineo TW et al., "Myeloid differentiation factor 88 is required for resistance to Neospora caninum infection," Vet Res. Jul.-Aug. 2009;40(4):32.

* cited by examiner

*Primary Examiner* — Mary Maille Lyons

(74) *Attorney, Agent, or Firm* — Maier & Maier, PLLC

(57) ABSTRACT

The present invention relates to a strain of *Neospora caninum* for use in treating cancer or infectious diseases.

11 Claims, 5 Drawing Sheets

*NEOSPORA* FOR USE IN TREATING CANCER AND INFECTIOUS DISEASES

FIELD OF INVENTION

The present invention particularly relates to the use of at least one strain of *Neospora caninum* or of a mutant thereof for treating cancer or infectious diseases in a subject in need thereof.

BACKGROUND OF INVENTION

Despite considerable progress using surgery, chemotherapy, and radiation to treat cancer, the 5-year survival rate for many cancers is still very low. An immune response directed to cancer cells may limit cancer development. However, tumor-mediated immunosuppression often blocks these antitumor responses. Therefore, a novel option suggested for treating cancer is to stimulate an effective immune response against tumor cells.

In the art, the possibility of using microorganisms as powerful adjuvants in the arsenal of anti-cancer immunotherapy has been recognized. Recent works highlighted the value of using attenuated microorganisms including virus, bacteria and parasites for treating cancer. For example, attenuated herpes virus expressing GM-CSF genetically modified to target tumor cells has been approved by the FDA for the treatment of metastatic melanomas (Amgen, IMLYGIC®). Moreover, attenuated microorganisms associated with another medicine are under clinical evaluation. For example, Opdivo® (nivolumab, IgG4 anti-PD1) associated to an attenuated bacterium Listeria monocytogenes is under clinical evaluation as an immunotherapy against non-small cell lung cancer. The combination of an attenuated virus modified to express antigens E6 and E7 from the human papillomavirus HPV16 (TG4001) with avelumab (IgG1 anti-PD-L1) is evaluated in phase 1-2 in the treatment of the head and neck cancers positives for HPV. Listeria monocytogenes that expresses mesotheline (CRS-207) associated with pembrolizumab (IgG4 anti-PD-1) is evaluated in phase 1 for the treatment of the gastric cancers.

*Neospora caninum* is an obligate intracellular protozoan parasite responsible for bovine neosporosis. Despite being taxonomically close to *Toxoplasma gondii, Neospora caninum* presents significant differences with this protozoan parasite. In particular,

*Neospora caninum* does not infect humans The life cycle of *Neospora caninum* is characterized by two distinct phases: (i) a sexual phase in the final host (canids and dogs in particular) which leads to the production of oocysts, container of the sporozoites, eliminated in deposit and (ii) an asexual phase in an intermediate host (such as, for example, sheep, goats, cattle, equidae, etc.) who leads to the production of tachyzoites, and then of cysts containing bradyzoites. The invasion process of the host cells by *Neospora caninum* comprises several stages leading to the formation of a parasitophorous vacuole in which the parasite multiplies and develops. Active entry and vacuole formation result from the coordinated secretion of parasite secretory organelles including rhoptries (ROP) and dense granules (GRA). The contents of these organelles are sequentially released during the lytic cycle and play a crucial role in the host-parasite interactions.

The inventors surprisingly showed that the administration of at least one strain of *Neospora caninum* to a subject induces a strong immune response, in particular against tumors. The present invention thus aims at providing a new treatment for cancer or infectious diseases based on the use of *Neospora caninum.*

SUMMARY

The present invention relates to at least one strain of *Neospora caninum* for use in treating cancer or an infectious disease. In one embodiment, the infectious disease is chronic. In one embodiment, said chronic infectious disease is selected from chronic virus infection and chronic bacterial infection. In another embodiment, said chronic infectious disease is a chronic parasite infection.

In one embodiment, the strain of *Neospora caninum* is a wild type strain.

In another embodiment, the strain of *Neospora caninum* is a mutant strain characterized by an over-expression of GRA15 protein, and/or by an under-expression of ROP16 protein.

In one embodiment, the strain of *Neospora caninum* is at a tachyzoite stage.

In one embodiment, the strain of *Neospora caninum* is for use in treating cancer, wherein cancer is a solid tumor, preferably an ovarian cancer, a pancreatic cancer or a melanoma.

In another embodiment, the strain of *Neospora caninum* is for use in treating an infectious disease, preferably a chronic infectious disease, wherein said infectious disease, preferably said chronic infectious disease, is associated with or induces an immunodepletion or immunosuppression, and is preferably selected from the group consisting of tuberculosis, HIV and malaria infections, preferably HIV or tuberculosis.

The present invention further relates to a composition for use in treating cancer or an infectious disease comprising the strain of *Neospora caninum* in association with an excipient. In one embodiment, the infectious disease is chronic. In one embodiment, said chronic infectious disease is selected from chronic virus infections and chronic bacterial infections. In another embodiment, said chronic infectious disease is a chronic parasite infection.

In one embodiment, the composition is a pharmaceutical composition and further comprises at least one pharmaceutically acceptable excipient.

In one embodiment, the composition is a vaccine composition for use in treating cancer or an infectious disease comprising the at least one strain of *Neospora caninum*, wherein preferably the vaccine composition comprises an adjuvant. In one embodiment, the infectious disease is chronic. In one embodiment, said chronic infectious disease is selected from chronic virus infections and chronic bacterial infections. In another embodiment, said chronic infectious disease is a chronic parasite infection.

In one embodiment, the strain of *Neospora caninum* for use, the composition for use or the vaccine composition for use as described in the present invention is to be administered to the subject via subcutaneous, intradermal or intratumoral routes.

In one embodiment, the amount of strains of *Neospora caninum* to be administered to the subject is ranging from about $10^4$ to about $10^{11}$.

The present invention further relates to a mutant strain of *Neospora caninum* characterized by an over-expression of GRA15 protein, and/or an under-expression of ROP16 protein.

The present invention also relates to a composition comprising the mutant strain of *Neospora caninum.*

The present invention further relates to a pharmaceutical composition comprising the mutant strain of *Neospora caninum* in association with at least one pharmaceutically acceptable excipient.

The present invention relates to a vaccine composition comprising the mutant strain of *Neospora caninum*, wherein preferably the vaccine composition comprises an adjuvant.

The present invention further relates to an ex vivo method for activating T cells, comprising contacting T cells with a strain of *Neospora caninum.*

Definitions

In the present invention, the following terms have the following meanings:

"Treatment" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject is successfully "treated" for the targeted pathologic condition or disorder if, after receiving a therapeutic amount of a strain of *Neospora caninum* as described herein, the subject shows observable and/or measurable improvement in one or more of the following: reduction in the number of pathogenic cells; reduction in the percent of total cells that are pathogenic; relief to some extent of one or more of the symptoms associated with the targeted pathologic condition or disorder; reduced morbidity and mortality, and/or improvement in quality of life issues. The above parameters for assessing successful treatment and improvement in the disease are readily measurable by routine procedures familiar to a physician.

"Therapeutically effective amount" refers to level or amount of agent that is aimed at, without causing significant negative or adverse side effects to the target, (1) delaying or preventing the onset of the targeted pathologic condition or disorder; (2) slowing down or stopping the progression, aggravation, or deterioration of one or more symptoms of the targeted pathologic condition or disorder; (3) bringing about ameliorations of the symptoms of the targeted pathologic condition or disorder; (4) reducing the severity or incidence of the targeted pathologic condition or disorder; (5) curing the targeted pathologic condition or disorder. An effective amount may be administered prior to the onset of the targeted pathologic condition or disorder, for a prophylactic or preventive action. Alternatively or additionally, the effective amount may be administered after initiation of the targeted pathologic condition or disorder, for a therapeutic action.

"Pharmaceutically acceptable excipient" refers to an excipient that does not produce an adverse, allergic or other untoward reaction when administered to an animal, preferably a human. It includes any and all dispersion media and solvents, coatings, isotonic and absorption delaying agents, additives, preservatives, stabilizers and the like. For human administration, preparations should meet sterility, pyrogenicity, general safety and purity standards as required by regulatory offices, such as, for example, FDA Office or EMA.

"Subject" refers to a mammal, preferably a human. In one embodiment, a subject may be a "patient", i.e., a warm-blooded animal, more preferably a human, who/which is awaiting the receipt of, or is receiving medical care or was/is/will be the object of a medical procedure, or is monitored for the development of a disease.

In one embodiment, the subject is an adult (for example a subject above the age of 18). In another embodiment, the subject is a child (for example a subject below the age of 18). In one embodiment, the subject is a male. In another embodiment, the subject is a female.

"About" preceding a figure means plus or less 10% of the value of said figure.

"Vaccine" refers to any preparation comprising substance or group of substances meant to induce an immune response in a subject, e.g., against a cancer cell, a tumor or against cells infected with an intracellular pathogen, such as, for example, *Mycobacterium tuberculosis*, HIV or plasmodium infected cells. As used herein, the term "vaccine" refers both to prophylactic vaccines and to therapeutic vaccines. Prophylactic vaccines are used to prevent a subject from the occurrence of a disease or condition (e.g., cancer or an infectious disease), or to limit the severity of the disease or condition, such that the subject administered with the vaccine only develops mild symptoms of the disease or condition. Therapeutic vaccines are intended to treat the targeted disease or condition, e.g., cancer or an infection disease, such as, for example, tuberculosis, HIV or malaria infections in a subject.

"Immunodepletion" or "immunosuppression" refer to a deficient immune system, i.e., an immune system for which one or more cell lines are either absent or deficient.

"Activated cells" refers to the state of an immune cell, in particular a T cell, that has been sufficiently stimulated to induce a detectable cellular response. Activation can also be associated with detectable effector function(s) such as cytokine production or suppressive activity.

"Autologous" refers to any material derived from the same individual to whom it is later to be re-introduced.

"Allogeneic" refers to any material derived from a different individual of the same specie as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

"Substantially purified" refers to a cell (e.g., a strain *Neospora caninum*) that is essentially free of other cell types or organisms (e.g., of other protozoan organisms). In one embodiment, a substantially purified strain refers to a strain which is at least about 75% free, 80% free, or 85% free, and preferably about 90%, 95%, 96%, 97%, 98%, or 99% free, from other cell types or organisms.

DETAILED DESCRIPTION

The present invention relates to a strain of *Neospora caninum* for use in treating cancer or an infectious disease in a subject in need thereof.

Indeed, the inventors have demonstrated that the administration of a strain of *Neospora caninum* can induce an immune response, for example, against a tumor or against cells infected with an intracellular pathogen, thereby allowing the treatment of the disease or condition.

*Neospora caninum* presents the advantage of being noninfectious in human. Moreover, *Neospora caninum* presents no risk of encystment that could lead to unpredictable side effects after several years of treatment.

Several strains of *Neospora caninum* have been described and are well known in the art. Examples of strains of *Neospora caninum* that may be used in the present invention include, but are not limited to, *Neospora caninum* 1 (NC-1), *Neospora caninum* Liverpool, BPA1, BPA6, NC-Beef, NC-Illinois, NC-LivB1, NC-LivB2, NC-SweB1, JAP1, NC-GER1, NC-GER2, NC-GER 3, NC-GER 4, NC-GER 5, NC-GER6, NC-GER8, NC-GER9, NC-Bahia, NC-Nowra, WA-K9, NcNZ1, NcNZ2, NcNZ3 and NcIs491. In one embodiment, the strain of *Neospora caninum* is *Neospora caninum* 1 (NC-1).

In one embodiment, the strain of *Neospora caninum* is a wild type strain.

In another embodiment, the strain of *Neospora caninum* is a mutant strain.

As used herein, a "mutant" strain is intended to mean a strain comprising at least one mutation as compared to the wild type strain from which it derives, wherein the term "mutation" may refer, without limitation, to point mutations, insertions, deletions, amplifications or gene duplications.

According to one embodiment of the invention, the mutant strain comprises a genome having at least about 70% identity with the genome of the wild type *Neospora caninum* strain from which it derives, preferably at least about 80%, 90%, 95%, 96%, 97%, 98% or 99% of identity.

Within the meaning of the present invention, the term "identity", when it is used in a relationship between the sequences of two or more nucleotide sequences, refers to the degree of relationship between these nucleotide sequences, as determined by the number of correspondences between the chains of two bases or more. According to the invention, "identity" corresponds to a percentage of identity between two sequences or more. This percentage is defined as a number of positions for which the bases are identical when the sequences are aligned optimally, divided by the total number of bases of the smaller of the two sequences. The differences between the sequences may be distributed at random and over all their lengths. Two sequences are said to be aligned optimally when the percentage of identity is maximal. Moreover, as will be clear to a person skilled in the art, it may be necessary to have recourse to additions of gaps so as to obtain an optimum alignment between the two sequences. The percentage of identity between two nucleic acid sequences can therefore be determined by comparing these two sequences aligned optimally in which the nucleic acid sequence to be compared may comprise additions or deletions compared with the reference sequence for optimum alignment between these two sequences. The percentage of identity is then calculated by determining the number of identical positions for which the nucleotide is identical between the two sequences, dividing this number of identical positions by the total number of positions in the comparison window and multiplying the result obtained by 100 in order to obtain the percentage identity between these two sequences. Preferably, the methods for determining identity are designed to give the greatest possible agreement between the compared sequences. The percentage identity can be determined by a particular mathematical model or by a computer program (generally designated by the term "algorithm"). Methods for calculating the identity between nucleotide sequences are well known to persons skilled in the art. Non-limitative examples of such methods include those described in the following documents: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48, 1073 (1988). Methods for determining identity have been described in computer programs accessible to the public. Preferred examples of methods using computer programs include, without being limited thereto, the GCG software, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is available from the National Center for Biotechnology Information (NCBI) and other sources (BLAST Manual, Altschul et al., NCB/NLM/NIH Bethesda, Md. 20894; Altschul et al., supra). The Smith-Waterman algorithm, which is well known to persons skilled in the art, can also be used to determine the percentage identity between two sequences.

In one embodiment, the mutant strain of *Neospora caninum* over-expresses GRA15.

As used herein, the term "GRA-15 protein" refers to "Dense Granule Protein 15" of *Neospora caninum*. The GRA15 protein is stored in secretory compartments of *Neospora caninum* (called dense granules) and secreted into the vacuole after host cell invasion. In one embodiment, GRA15 refers to the homologue in *Neospora caninum* of the GRA15 gene of *Toxoplasma gondii* (having the accession number: Gene ID: 7895856, locus tag TGME49_275470).

As used herein, the term "over-expression" refers to an increased expression level as compared to a reference expression level, such as, for example, an expression level superior or equal to 110%, 120%, 130%, 140%, 150%, 160%, 170%, 180%, 190%, 200%, 300%, 400%, 500%, 600%, 700%, 800% 900% or 1000% or more of the reference expression level.

Methods to obtain a cell over-expressing a protein are well known in the art. For example, an over-expression of a protein may be obtained by constructing a "knock-in" of the gene encoding this protein. Examples of methods for constructing a knock-in include, but are not limited to, electroporation, lipofection, calcium phosphate transfection and the like.

As used herein, the term "expression level" can refer alternatively to the transcription level of a gene (i.e., expression is measured at the RNA level) or to the translation level of the gene (i.e., expression is measured at the protein level).

Methods for assessing the transcription level of a gene are well known in the prior art. Examples of such methods include, but are not limited to, RT-PCR, RT-qPCR, Northern Blot, hybridization techniques such as, for example, use of microarrays, and combination thereof including but not limited to, hybridization of amplicons obtained by RT-PCR, sequencing such as, for example, next-generation DNA sequencing (NGS) or RNA-seq (also known as "Whole Transcriptome Shotgun Sequencing") and the like.

Methods for determining a protein level in a sample are well-known in the art. Examples of such methods include, but are not limited to, immunohistochemistry, Multiplex methods (Luminex), Western blot, enzyme-linked immunosorbent assay (ELISA), sandwich ELISA, fluorescent-linked immunosorbent assay (FLISA), enzyme immunoassay (EIA), radioimmunoassay (RIA), flow cytometry (FACS) and the like.

In one embodiment, the reference expression level (which may correspond to a reference protein expression level or a reference mRNA expression level as hereinabove described) corresponds to the expression level measured in a reference *Neospora caninum* strain, preferably in a wild type *Neospora caninum* strain.

In another embodiment, the mutant strain of *Neospora caninum* underexpresses ROP16, preferably the mutant strain does not express ROP16 protein. For example, the mutant strain of *Neospora caninum* is a knockout mutant for the gene encoding for ROP16 proteins)(ROP16$^{KO}$).

As used herein, the term "ROP16 protein" refers to "Rhoptry Protein 16". In one embodiment, ROP16 refers to the homologue in *Neospora caninum* of the ROP16 gene of *Toxoplasma gondii* (having the accession number: Gene ID: 7894782).

As used herein, the term "under-expression" (or down-expression) refers to a decreased expression level as compared to a reference expression level, such as, for example, an expression level inferior or equal to 90%, 80%, 70%, 60%, 50%, 40%, 30%, 20%, 10%, or less of the reference expression level, preferably of the expression level measured in a wild type *Neospora caninum* strain.

As used herein, the term "knockout for the gene" denotes a genetic mutation resulting in a loss of function and/or a loss of expression of the protein encoded by the said gene. In one embodiment, said genetic mutation corresponds to the disruption of all or a portion of a gene of interest, preferably the total disruption of the gene. Preferably, the deletion starts at or before the start codon of the deleted gene, and ends at or after the stop codon of the deleted gene. Other examples of genetic mutations include, but are not limited to, substitution, deletion, or insertion.

In one embodiment, the knockout of ROP16 protein can be achieved by replacing the coding sequence with a nucleic acid molecule encoding a selectable marker, replacing the coding sequence with a nucleic acid molecule encoding an exogenous protein, substituting the promoter with a mutated promoter which can no longer be recognized by *Neospora caninum* transcription proteins (i.e., a promoter mutation), etc.

In one embodiment, the mutant strain of *Neospora caninum* over-expresses GRA15 and under-expresses ROP16.

In one embodiment, the strain of *Neospora caninum* is isolated, in particular is isolated from its natural environment.

In one embodiment, the strain of *Neospora caninum* is substantially purified.

In one embodiment, a living strain of *Neospora caninum* is used in the present invention.

In one embodiment, the strain of *Neospora caninum* is a tachyzoite. By "tachyzoite" is meant the rapidly multiplying form of *Neospora caninum*. The tachyzoite has usually a crescent shape and a variable size, for example a size of about 5-8×2-3 μm. The apical part of the parasite comprises conoids which participate in the penetration of the parasite into the host cell. The micronemes, the rhoptries and the dense granules constitute the three major organelles of the tachyzoite, which also comprises a nucleus, an apicoplast, a Golgi apparatus, an endoplasmic reticulum and an organite similar to the mitochondrion.

In one embodiment, the strain of *Neospora caninum* is a tachyzoite from *Neospora caninum*-1 (NC-1).

Methods for obtaining and maintaining living strains, in particular tachyzoites, of *Neospora caninum* are well known by the skilled artisan. An example of a method for maintaining strains of *Neospora caninum* is indicated below.

Tachyzoites of the NC-1 strain of *Neospora caninum* are harvested from infected human foreskin fibroblasts (such as, for example, Hs 27 (ATCC CRL-1634) cultured in monolayers in DMEM, supplemented with 10% heat-inactivated FCS, 50 U/ml penicillin/50 μg/ml streptomycin, and 1% HEPES). *Neospora caninum* tachyzoites may be harvested when monolayers of human foreskin fibroblasts are completely lysed.

In one embodiment, *Neospora caninum* is for treating cancer.

In one embodiment, *Neospora caninum* is for treating a tumor, preferably a solid tumor. Indeed, the Inventors have shown that the administration of *Neospora caninum* induces a decrease of the tumor volume in mice (see Examples). Therefore, in one embodiment, *Neospora caninum* is for inducing a decrease of the tumor volume and/or for preventing an increase of the tumor volume in a subject in need thereof.

In one embodiment, the cancer may be any solid tumor. Examples of solid tumors include but are not limited to, bile duct cancer (e.g., periphilar cancer, distal bile duct cancer, intrahepatic bile duct cancer), bladder cancer, bone cancer (e.g., osteoblastoma, osteochrondroma, hemangioma, chondromyxoid fibroma, osteosarcoma, chondrosarcoma, fibrosarcoma, malignant fibrous histiocytoma, giant cell tumor of the bone, chordoma, lymphoma, multiple myeloma), brain and central nervous system cancer (e.g., meningioma, astocytoma, oligodendrogliomas, ependymoma, gliomas, medulloblastoma, ganglioglioma, Schwannoma, germinoma, craniopharyngioma), breast cancer (e.g., ductal carcinoma in situ, infiltrating ductal carcinoma, infiltrating lobular carcinoma, lobular carcinoma in, situ, gynecomastia), Castleman disease (e.g., giant lymph node hyperplasia, angio follicular lymph node hyperplasia), cervical cancer, colorectal cancer, endometrial cancer (e.g., endometrial adenocarcinoma, adenocanthoma, papillary serous adnocarcinroma, clear cell), esophagus cancer, gallbladder cancer (e.g., mucinous adenocarcinoma, small cell carcinoma), gastrointestinal carcinoid tumors (e.g., choriocarcinoma, chorioadenoma destruens), Hodgkin's disease, non-Hodgkin's lymphoma, Kaposi's sarcoma, kidney cancer (e.g., renal cell cancer), laryngeal and hypopharyngeal cancer, liver cancer (e.g., hemangioma, hepatic adenoma, focal nodular hyperplasia, hepatocellular carcinoma), lung cancer (e.g., small cell lung cancer, non-small cell lung cancer), mesothelioma, plasmacytoma, nasal cavity and paranasal sinus cancer (e.g., esthesioneuroblastoma, midline granuloma), nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma (e.g., embryonal rhabdomyosarcoma, alveolar rhabdomyosarcoma, pleomorphic rhabdomyosarcoma), salivary gland cancer, skin cancer (e.g., melanoma, nonmelanoma skin cancer), stomach cancer, testicular cancer (e.g., seminoma, nonseminoma germ cell cancer), thymus cancer, thyroid cancer (e.g., follicular carcinoma, anaplastic carcinoma, poorly differentiated carcinoma, medullary thyroid carcinoma, thyroid lymphoma), vaginal cancer, vulvar cancer, and uterine cancer (e.g., uterine leiomyosarcoma).

In one embodiment, the cancer is selected from ovarian cancer, pancreatic cancer and melanoma.

In one embodiment, the cancer is glioma.

In one embodiment, *Neospora caninum* is for treating metastatic cancer. In one embodiment, *Neospora caninum* is for preventing the occurrence of metastasis, and/or for reducing the number of metastasis in a subject in need thereof.

In one embodiment, *Neospora caninum* is for treating blood cancer. In one embodiment, *Neospora caninum* is for treating an infectious disease.

In one embodiment, said infectious disease is a chronic infectious disease, i.e., a disease due to the prolonged and persistent invasion of the body of a subject by pathogens (including, for example, parasites, bacteria (in particular mycobacteria) and viruses).

In one embodiment, said infectious disease is a chronic virus infection, such as, for example, a HIV infection.

In one embodiment, said infectious disease is a chronic bacterial infection, such as, for example, an infection by *Mycobacterium tuberculosis*.

In one embodiment, said infectious disease is a chronic infection with a parasite, such as, for example, an infection by plasmodium.

In one embodiment, said chronic infectious disease is caused by the presence of an intracellular pathogen, such as, for example, an intracellular virus, an intracellular bacterium or an intracellular parasite.

In one embodiment, said infectious disease is a chronic infectious disease associated with an immunodepletion or an immunosuppression or inducing an immunodepletion or an immunosuppression.

Examples of chronic infectious diseases associated with or inducing an immunodepletion or an immunosuppression include, but are not limited to, tuberculosis, HIV or malaria infections.

In one embodiment, said infectious disease is not due to an apicomplexan of the family Cryptosporidiidae. In one embodiment, said infectious disease is not a cryptosporidiosis. In one embodiment, said infectious disease is not neosporosis.

In one embodiment, the subject is a human.

In one embodiment, the subject is immunosuppressed, i.e., presents an impaired immune system. In one embodiment, the immune system of the subject has compromised ability to fight a cancer or an infectious disease.

In one embodiment, the subject has cancer. In one embodiment, the subject is diagnosed or has been diagnosed with cancer.

In one embodiment, the cancer is early or late stage cancer.

In one embodiment, the subject was not treated previously with another treatment for cancer (i.e., the method of the invention is the first line treatment).

In another embodiment, the subject previously received one, two or more other treatments for cancer (i.e., the method of the invention is a second line, a third line or more). In one embodiment, the subject previously received one or more other treatments for cancer, but was unresponsive or did not respond adequately to these treatments, which means that there is no or too low therapeutic benefit induced by these treatments.

In another embodiment, the subject is at risk of developing cancer. Examples of risk factors for developing cancer include, but are not limited to, family history of cancer, genetic predisposition, or exposure to a carcinogen.

In another embodiment, the subject has an infectious disease, preferably a chronic infectious disease. In one embodiment, the subject has an infectious disease (preferably a chronic infectious disease) associated with or inducing an immunodepletion or an immunosuppression. In one embodiment, the subject has a chronic infectious disease caused by an intracellular pathogen. In one embodiment, the subject has a tuberculosis infection. In another embodiment, the subject has an HIV infection. In another embodiment, the subject has a malaria infection.

In one embodiment, the subject was not treated previously with another treatment for the said infection (i.e., the method of the invention is the first line treatment).

In another embodiment, the subject previously received one, two or more other treatments for the said infection (i.e., the method of the invention is a second line, a third line or more). In another embodiment, the subject previously received one or more other treatments for the said infection, but was unresponsive or did not respond adequately to these treatments, which means that there is no or too low therapeutic benefit induced by these treatments.

In one embodiment, the subject is not affected by a cryptosporidiosis.

The present invention further relates to a composition for use in treating cancer or infectious diseases in a subject in need thereof comprising, consisting or consisting essentially of at least one strain of *Neospora caninum* or a mutant thereof as described hereinabove.

As used herein, "consisting essentially of", with reference to a composition, means that at least one strain of *Neospora caninum* or a mutant thereof of the invention is the only one therapeutic agent or agent with a biologic activity within said composition.

Another object of the invention is a pharmaceutical composition for use in treating cancer or infectious diseases in a subject in need thereof comprising, consisting or consisting essentially of at least one strain of *Neospora caninum* or a mutant thereof as described hereinabove and at least one pharmaceutically acceptable excipient.

Examples of pharmaceutically acceptable excipients include, but are not limited to, media, solvents, coatings, isotonic and absorption delaying agents, additives, stabilizers, preservatives, surfactants, substances which inhibit enzymatic degradation, alcohols, pH controlling agents, and propellants.

Examples of pharmaceutically acceptable media include, but are not limited to, water, phosphate buffered saline, normal saline or other physiologically buffered saline, or other solvent such as glycol, glycerol, and oil such as olive oil or an injectable organic ester. A pharmaceutically acceptable medium can also contain liposomes or micelles, and can contain immunostimulating complexes prepared by mixing polypeptide or peptide antigens with detergent and a glycoside.

Examples of coating materials include, but are not limited to, lecithin.

Examples of isotonic agents include, but are not limited to, sugars, sodium chloride, and the like. Examples of agents that delay absorption include, but are not limited to, aluminum monostearate and gelatin.

Examples of additives include, but are not limited to, mannitol, dextran, sugar, glycine, lactose or polyvinylpyrrolidone or other additives such as antioxidants or inert gas, stabilizers or recombinant proteins (e.g., human serum albumin) suitable for in vivo administration.

Examples of suitable stabilizers include, but are not limited to, sucrose, gelatin, peptone, digested protein extracts such as NZ-Amine or NZ-Amine AS.

Another object of the invention is a medicament for use in treating cancer or infectious diseases in a subject in need thereof comprising, consisting or consisting essentially of at least one strain of *Neospora caninum* or a mutant thereof as described herein.

Another object of the invention is a vaccine composition for use in treating cancer or infectious diseases in a subject in need thereof comprising, consisting or consisting essentially of at least one strain of *Neospora caninum* or a mutant thereof as described herein. In one embodiment, the vaccine of the invention is a prophylactic vaccine. In another embodiment, the vaccine of the invention is a therapeutic vaccine.

In one embodiment, the vaccine composition further comprises at least one adjuvant.

As used herein, the term "adjuvant" refers to a substance that enhances, augments or potentiates the host's immune response induced by the strain of *Neospora caninum.*

Examples of adjuvants that can be used in the vaccine composition include, but are not limited to, ISA51; emulsions such as CFA, MF59, montanide, AS03 and AF03; mineral salts such as alum, calcium phosphate, iron salt, zirconium salt, and AS04; TLR ligands such as TLR2 ligands (such as outer-surface protein A or OspA), TLR3 ligands (such as poly I:C), TLR4 ligands (such as MPL and GLA), TLR5 ligands, TLR7/8 ligands (such as imiquimod), TLR9 ligands (such as CpG ODN); polysacharrides such as chitin, chitosan, α-glucans, β-glucans, fructans, mannans, dextrans, lentinans, inulin-based adjuvants (such as gamma inulin); TLR9 and STING ligands such as K3 CpG and cGAMP.

The strain of *Neospora caninum*, the composition, the pharmaceutical composition, the medicament or the vaccine composition of the present invention may be administered orally, parenterally, by intraperitoneal administration, by inhalation spray, topically, rectally, nasally, buccally, vaginally or via an implanted reservoir.

In one embodiment, the strain of *Neospora caninum*, the composition, the pharmaceutical composition, the medicament or the vaccine composition of the present invention is injected. Examples of injections include, but are not limited to, intratumoral, intradermal, subcutaneous, intravenous, intramuscular, intra-lymphatic, intra-articular, intra-synovial, intrasternal, intrathecal, intravesical, intrahepatic, intralesional and intracranial injection or infusion techniques.

In one embodiment, the strain of *Neospora caninum* is administered subcutaneously. In one embodiment, the strain of *Neospora caninum* is administered intradermally. In one embodiment, the strain of *Neospora caninum* is administered intratumorally.

In one embodiment, the strain, the composition, the pharmaceutical composition, the medicament or the vaccine composition of the present invention is in a form adapted to oral administration. According to a first embodiment, the form adapted to oral administration is a solid form selected from the group comprising tablets, pills, capsules, soft gelatin capsules, sugarcoated pills, orodispersing tablets, effervescent tablets or other solids. According to a second embodiment, the form adapted to oral administration is a liquid form, such as, for example, a drinkable solution, a buccal spray, liposomal forms and the like.

In another embodiment, the strain, the composition, the pharmaceutical composition, the medicament or the vaccine composition of the present invention is formulated for rectal or vaginal administration and may be presented as suppositories, pessaries, tampons, creams, gels, pastes, foams or sprays.

In another embodiment, the strain, the composition, the pharmaceutical composition, the medicament or the vaccine composition of this invention is in a form suitable for parenteral administration. Forms suitable for parenteral administrations include, but are not limited to, sterile isotonic aqueous or non-aqueous solutions, dispersions, suspensions or emulsions, or sterile powders which may be reconstituted into sterile injectable solutions or dispersions just prior to use.

In another embodiment, the strain, the composition, the pharmaceutical composition, the medicament or the vaccine composition of the invention is in a form adapted for local delivery via the nasal and respiratory routes. Examples of formulations suitable for nasal or respiratory administration include, but are not limited to, nasal solutions, sprays, aerosols and inhalants.

In another embodiment, the strain, the composition, the pharmaceutical composition, the medicament or the vaccine composition of the invention is in a form adapted to a topical administration. Examples of formulations adapted to a topical administration include, but are not limited to, ointment, paste, eye drops, cream, patch, such as, for example, transdermal patch, gel, liposomal forms and the like.

In one embodiment, the composition or formulation of the invention may be presented in unit-dose or multi-dose sealed containers, for example, ampoules and vials, and may be stored in a lyophilized condition requiring only the addition of the sterile liquid excipient, for example water for injection, immediately prior to use. Extemporaneous injection solutions and suspensions may be prepared from sterile powders, granules and tablets.

The exact dose for administration can be determined by the skilled practitioner, in light of factors related to the subject that requires treatment. Dosage is adjusted to provide sufficient levels of the composition or to maintain the desired effect of reducing signs or symptoms of the targeted pathologic condition or disorder, or reducing severity of the targeted pathologic condition or disorder. Factors which may be taken into account include the severity of the disease state (such as for example the tumor volume or the number of infected cells), the prognosis of the disease, the localization or accessibility to the tumor, general health of the subject, age, weight, and gender of the subject, diet, time and frequency of administration, drug combination(s), reaction sensitivities, and tolerance/response to therapy.

In one embodiment, a therapeutically effective amount of the strain, the composition, the pharmaceutical composition, the medicament or the vaccine composition of the present invention is administered (or is to be administered) to the subject.

In one embodiment of the invention, the strain of *Neospora caninum* or the composition, the pharmaceutical composition, the medicament or the vaccine composition is administered at least once, preferably at least twice, more preferably at least three times, and even more preferably at least four times at day, week or month intervals, according to a prime/boost mode.

In one embodiment of the invention, the amount of strains of *Neospora caninum* (preferably of tachyzoites) as described hereinabove administered per administration ranges from about $10^4$ to about $10^{11}$, preferably from about $10^5$ to about $10^{10}$, more preferably from about $10^6$ to about $10^9$, and even more preferably from about $10^7$ to about $10^8$.

In one embodiment of the invention, the daily amount of strains of *Neospora caninum* (preferably of tachyzoites) as described hereinabove administered per day ranges from about $10^4$ to about $10^{11}$ per day, preferably from about $10^5$ to about $10^{10}$/day, more preferably from about $10^6$ to about $10^9$/day, and even more preferably from about $10^7$ to about $10^8$/day.

The present invention further relates to a method for treating cancer or an infectious disease in a subject in need thereof, comprising administering to the subject a therapeutically effective amount of a strain of *Neospora caninum* or mutant thereof.

In one embodiment, the method of the invention is a method for decreasing tumor volume, and/or for preventing any increase of tumor volume.

In one embodiment, the method of the invention is for preventing the occurrence of metastasis, and/or for reducing the number of metastasis.

The present invention relates to a method for inducing an immune response against a cancer cell, a tumor or an infected cell, preferably a cell infected with an intracellular pathogen, such as, for example, *Mycobacterium tuberculosis*, HIV or plasmodium in a subject in need thereof. In one embodiment, the immune response is a non-specific response. In one embodiment, the immune response is characterized by the secretion of IFNγ.

As used herein, "an immune response" is a detectable immune response e.g., T cell immune response or antibody production. Methods for measuring a T cell immune response are well known by the skilled artisan and include, without limitation, monitoring the production of IFN-gamma.

The Inventors show herein that the administration to a subject of strains of *Neospora caninum* is able to induce cellular and humoral immune responses. Indeed, the Inventors show a four-fold increase secretion of IFNgamma after *Neospora caninum* administration and specific IgG against *Neospora caninum* are detected in the serum after *Neospora caninum* administration (see Examples).

The present invention thus relates to a method for inducing a cellular and/or humoral immune response in a subject, wherein said method comprises administering to the subject at least one cell of the strain of *Neospora caninum* to the subject.

The present invention relates to a method for inducing a decrease of the tumor volume, preferably a decrease of the tumor volume of at least 25%, preferably at least 30%, 40%, 50%, 60%, 70%, 80%, 90% or more, wherein said method comprises administering to the subject at least one cell of the strain of *Neospora caninum* to the subject.

Indeed, the Inventors show herein that the administration of strains of *Neospora caninum* leads to the decrease of the tumor volume. More specifically, a 3-fold decrease of the tumor volume is observed after a peritumoral administration (see Examples).

The present invention further relates to an ex vivo method for activating cells, comprising contacting cells, preferably human cells, more preferably PBMC (peripheral blood mononuclear cells) and even more preferably T cells, with a strain of *Neospora caninum* as described in the present invention.

The present invention thus further relates to the use of a strain of *Neospora caninum* as described in the present invention for ex vivo activating cells, preferably human cells, more preferably PBMC and even more preferably T cells, wherein said cells are contacted with said strain of *Neospora caninum.*

In one embodiment, said cells are recovered from a patient with cancer or with an infectious disease. In one embodiment, the step of recovering the cells from a patient is not part of the method of the invention.

In one embodiment, the activated cells are to be administered to a patient with cancer or with an infectious disease, thereby treating cancer or an infectious disease. In one embodiment, the activated cells are autologous to the cells of the patient. In another embodiment, the activated cells are allogenic to the cells of the patient.

The present invention further relates to a method for treating cancer or an infectious disease in a subject in need thereof, comprising:

- contacting cells, preferably PBMC, more preferably T cells with a strain of *Neospora caninum* as described in the present invention, wherein preferably said cells are previously recovered from said subject, and
- administering the activated cells to the subject, thereby treating cancer or an infectious disease.

Another object of the invention is a mutant strain of *Neospora caninum*, wherein said mutant strain overexpresses GRA15 and/or under-expresses ROP16.

Examples of strains of *Neospora caninum* from which the mutant strain may derive include, but are not limited to, *Neospora caninum* 1 (NC-1), *Neospora caninum* Liverpool, BPA1, BPA6, NC-Beef, NC-Illinois, NC-LivB1, NC-LivB2, NC-SweB1, JAP1, NC-GER1, NC-GER2, NC-GER 3, NC-GER 4, NC-GER 5, NC-GER6, NC-GER8, NC-GER9, NC-Bahia, NC-Nowra, WA-K9, NcNZ1, NcNZ2, NcNZ3 and NcIs491. In one embodiment, the mutant strain of *Neospora caninum* derives from wild type *Neospora caninum*-1 (NC-1). In another embodiment, the mutant strain of *Neospora caninum* derives from wild type *Neospora caninum* Liverpool.

In one embodiment of the invention, the mutant strain comprises a genome having more than 70% identity with the genome of the wild type strain of *Neospora caninum* from which it derives, preferably more than 80%, 90%, 95%, 96%, 97%, 98% or 99% of identity.

In one embodiment, the mutant strain of *Neospora caninum* over-expresses GRA15.

In another embodiment, the mutant strain of *Neospora caninum* under-expresses ROP16, preferably the mutant strain does not express ROP16 protein. For example, the mutant strain of *Neospora caninum* is a knockout mutant for the gene encoding for ROP16 proteins)($ROP16^{KO}$).

In one embodiment, the knockout of ROP16 protein can be achieved by replacing the coding sequence with a nucleic acid molecule encoding a selectable marker, replacing the coding sequence with a nucleic acid molecule encoding an exogenous protein, substituting the promoter with a mutated promoter which can no longer be recognized by *Neospora caninum* transcription proteins (i.e., a promoter mutation), etc.

In one embodiment, the mutant strain of *Neospora caninum* over-expresses GRA15 and under-expresses ROP16.

Another object of the present invention is a composition comprising, consisting or consisting essentially of at least one mutant strain of *Neospora caninum* as described hereinabove.

Another object of the invention is a pharmaceutical composition comprising, consisting or consisting essentially of at least one mutant strain of *Neospora caninum* as described hereinabove and at least one pharmaceutically acceptable excipient.

Examples of pharmaceutically acceptable excipients are described herein.

Another object of the invention is a medicament comprising, consisting or consisting essentially of at least one mutant strain of *Neospora caninum* as described hereinabove.

Another object of the invention is a vaccine composition comprising, consisting or consisting essentially of at least one mutant strain of *Neospora caninum* as described hereinabove.

In one embodiment, the vaccine composition further comprises at least one adjuvant.

EXAMPLES

Figure 1:
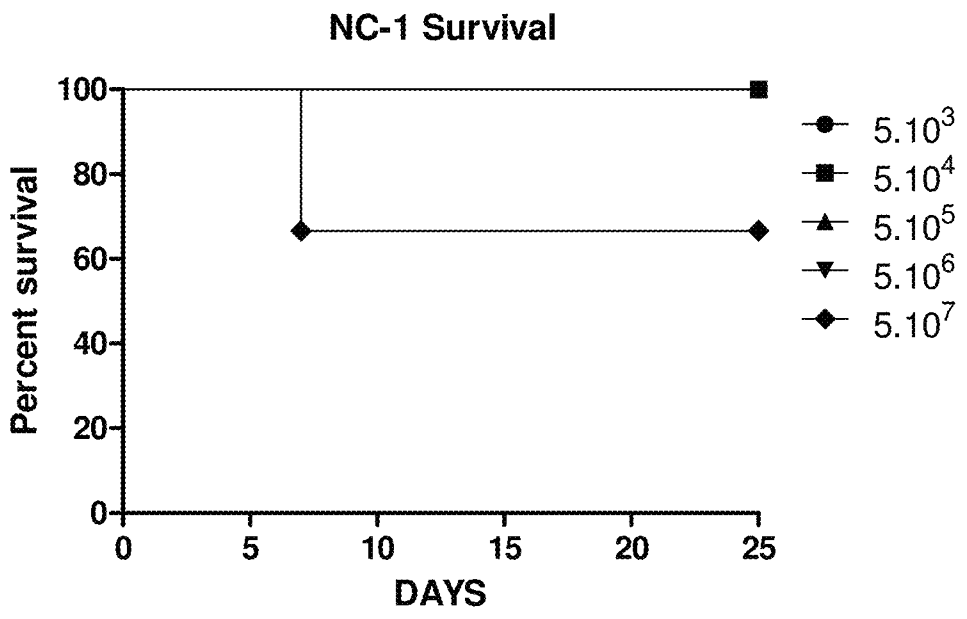
FIG. 1 is a dose-response curve showing the percent survival of mice after the administration of different doses of wild type strains of *Neospora caninum*-1 (NC-1).

Example 1: In Vivo Effect of *Neospora caninum*

Materials And Methods

Mice

Eight week-old female inbred C57BL/6 mice are maintained under pathogen-free conditions.

*Neospora caninum*-1 Strain

Tachyzoites of the NC-1 strain of *Neospora caninum* are harvested from infected human foreskin fibroblasts Hs 27 (ATCC CRL-1634) cultured in monolayers in DMEM, supplemented with 10% heat-inactivated FCS, 50 U/ml penicillin/50 μg/ml streptomycin, and 1% HEPES. *Neospora caninum* tachyzoites may be harvested when monolayers of human foreskin fibroblasts are completely lysed.

Tumor Cells

EG7 cells (EL4-OVA thymoma cells transfected with chicken albumin cDNA) are cultured, for example, in RPMI medium, with $5\times10^5$ M of 2-mercaptoethanol, 50 UI/mL of penicillin and 50 mg/mL of streptomycin.

Tumor Cell Inoculations $1\times10^5$ live EG7 cells are inoculated intradermally in the right flank of the mice. Tumor diameters are measured 3 times weekly, and mice are euthanized when tumor diameters reached 25.000 $mm^3$.

*Neospora caninum*-1 (NC-1) Administration

Mice are injected subcutaneously in the right flank at day 4 and again at day 7 with $5\times10^6$ freshly isolated tachyzoites of NC-1 strain of *Neospora caninum.*

Cell Culture Conditions and Cytokine Quantification

Spleens are harvested and pressed through a stainless steel mesh. Single cell suspensions are obtained by filtration through a nylon mesh to remove tissue debris.

Spleen erythrocytes are lysed by hypotonic shock, single cells of spleen are resuspended in RPMI 1640 supplemented with 5% FCS, HEPES (25 mM), L-glutamine (2 mM), sodium pyruvate (1 mM), β-mercaptoethanol ($5\times10^{-5}$ M) and penicillin (50 U/ml)/streptomycin (50 μg/ml). Spleen cells are cultured in 96-well plates at $5\times10^5$ cells per well, in 200 μl of culture medium, alone or containing concanavalin A (10 μg/ml). The plates are incubated for 72 hours in 5% CO2 at 37° C. Cell culture supernatants are harvested and kept at −20° C. IFN-gamma quantification is determined by an ELISA assay on the supernatant of the spleen lymphocytes.

Results

*Neospora caninum* Infection is Lethal at Very High Inoculum Doses

Strains of *Neospora caninum* challenging study reveals that all mice immunized with $5\times10^6$, $5\times10^5$, $5\times10^4$, and $5\times10^3$ of NC-1 tachyzoites survive up to 25 days. One on three mice infected with 5x10' NC−1 tachyzoites succumbs on day 5 (FIG. 1).

*Neospora caninum* Induces Humoral and Cellular Immune Responses

Figure 2:
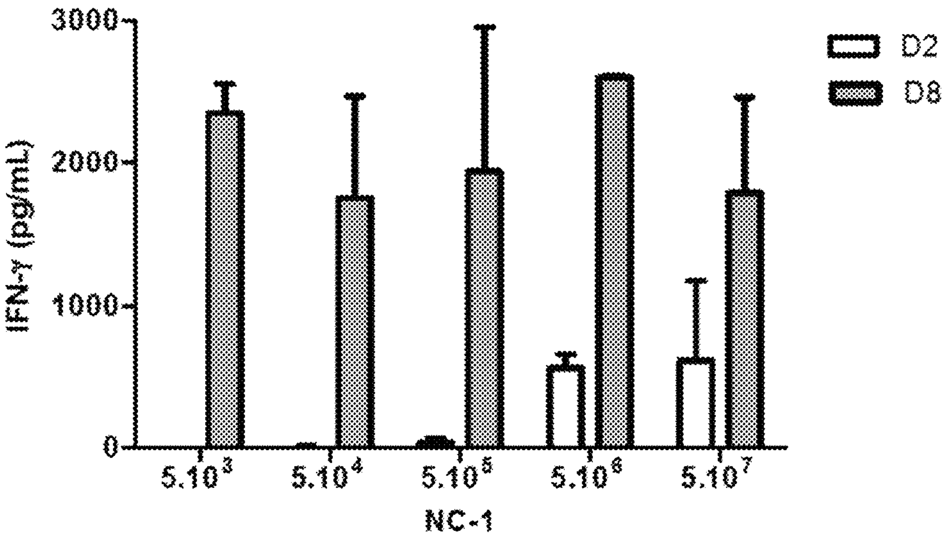
FIG. 2 is a histogram showing the seric IFNgamma production at day 2 or day 8 after administration of different doses of wild type strains of *Neospora caninum*-1 (NC-1) in mice.

High levels of seric IFN-gamma (approximatively 2000 pg/mL) are obtained at day 8 post-infection whatever the doses of injected NC-1 tachyzoites. IFN-gamma secretion at day 2 post-infection is only observed in serum of mice infected with $5\times10^7$ and $5\times10^6$ NC-1 tachyzoites (FIG. 2).

Figure 3:
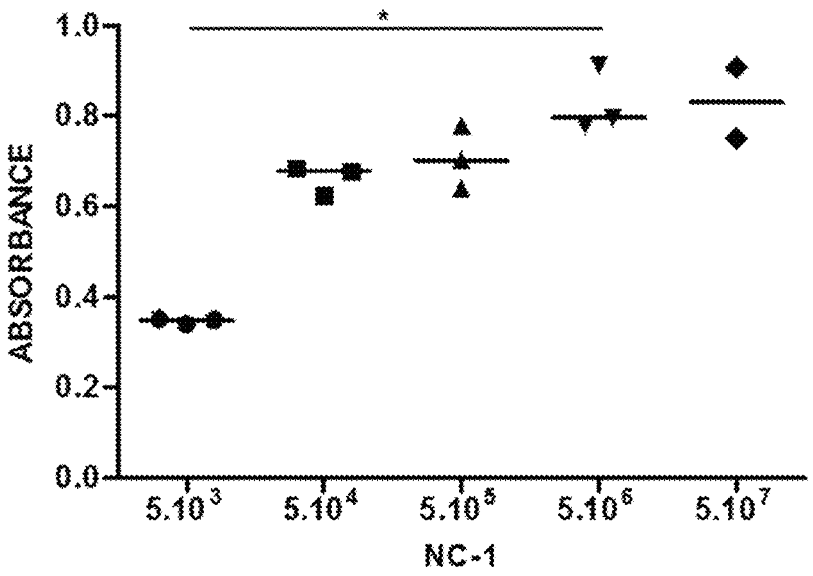
FIG. 3 is a dot plot showing the production of specific IgG against *Neospora caninum* after administration of different doses of wild type strains of *Neospora caninum*-1 (NC-1) in mice.

All infected mice develop *Neospora*-specific humoral immune responses at day 21 post-infection. As shown in FIG. 3, highest levels of humoral antibodies are achieved in mice infected with $5\times10^7$ and $5\times10^6$ NC-1 tachyzoites (approximatively 0.8 for a dilution 1/50) (FIG. 3).

According to these results showing a correlation between the dose and the anti-*Neospora* immune response, it was decided to focus on the concentration of $5\times10^6$ NC-1 tachyzoites for the next experiments.

Figure 4:
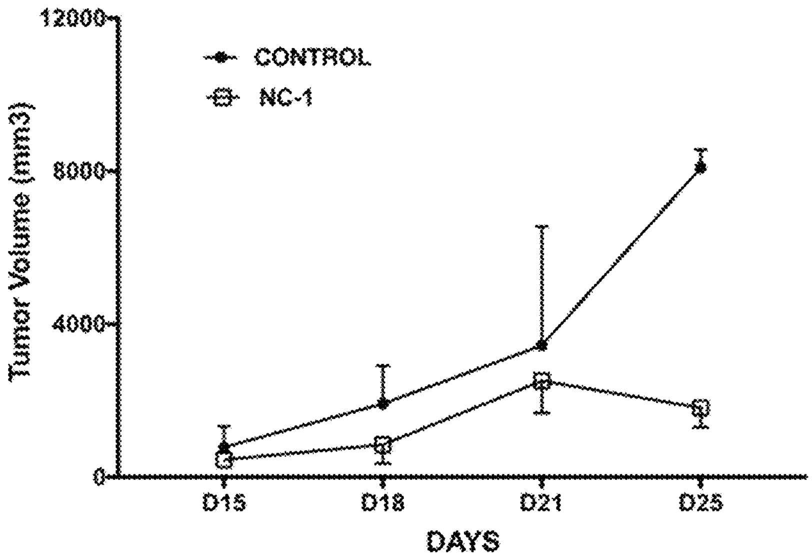
FIG. 4 is a curve showing the tumor volume of mice inoculated with tumor cells and treated with wild type strains of *Neospora caninum*-1 (NC-1) compared to untreated mice inoculated with the tumor only (control).
Figure 5:
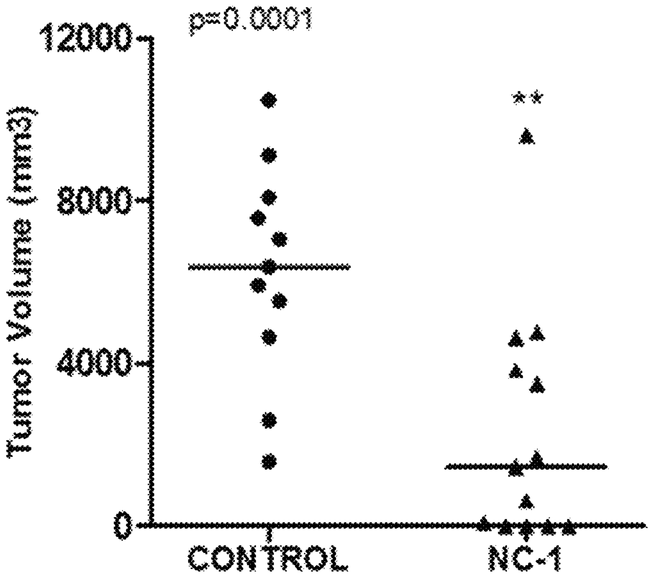
FIG. 5 is a dot plot showing the tumor volume of mice inoculated with tumor cells and treated with wild type strains of *Neospora caninum*-1 (NC-1) compared to untreated mice inoculated with the tumor only (control) at day 25. **: p-value <0.01 (Kruskall Wallis test).

*Neospora caninum* Treatment Suppresses and/or Regresses an Established Solid Tumor Development Mice that received EG7 cells develop large tumors (8090±507 $mm^3$) at day 25 post transfer. In contrast, pretreatment with NC-1 tachyzoites significantly reduces the tumor volume (1816±465 $mm^3$), demonstrating that NC-1 tachyzoites suppress the thymome tumor development (FIGS. 4 and 5).

Figure 6:
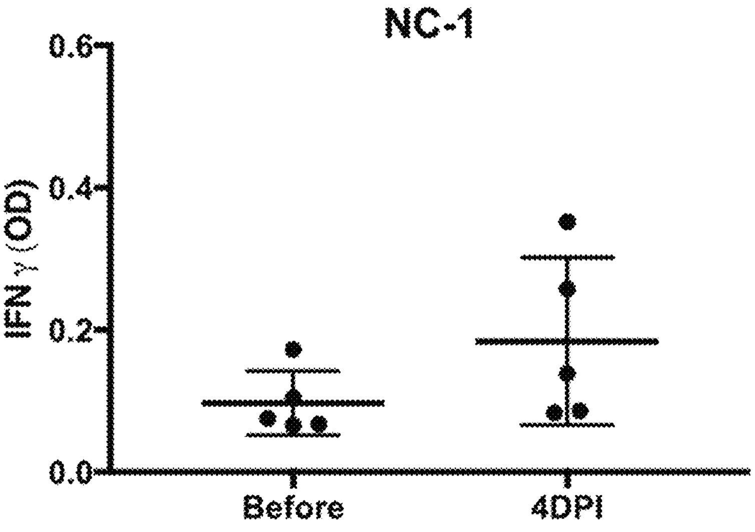
FIG. 6 is a dot plot showing the serum level of IFNgamma before or 4 days post-infection (4 DPI) with wild type strains of *Neospora caninum*-1 in mice implanted with the tumor.

*Neospora caninum* Induces a Protective Immune Response Against Tumor Development An increase of serum level of IFN-gamma 8 days post tumor implantation and 4 days after the first *Neospora* dose inoculation (4 DPI) is observed in *Neospora*-treated mice compared to serum level of IFN-gamma in untreated mice (FIG. 6).

Figure 7:
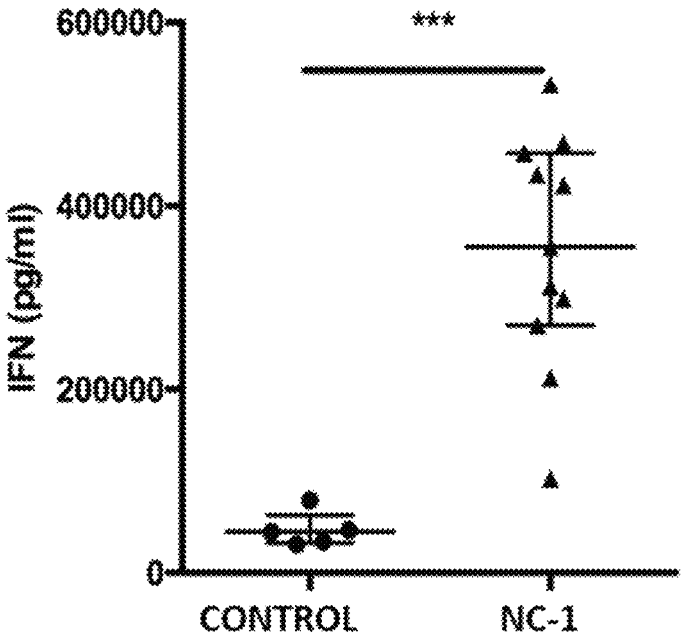
FIG. 7 is a dot plot showing the in vitro IFNgamma production by spleen lymphocytes recovered from mice treated with wild type strains of *Neospora caninum*-1 (NC-1) or untreated (Control) and stimulated with concanavalin A (ConA).

An increase of IFN-gamma production is observed in vitro by spleen lymphocytes recovered from *Neospora*-treated mice (NC-1) and stimulated with concanavalin A compared to stimulated spleen lymphocytes recovered from untreated mice (control). This result suggests that *Neospora caninum* generates a therapeutic antitumor immune response by reversing spleen immunosuppression during tumor development (FIG. 7).

Example 2: *Neospora caninum* Over-Expressing GRA15II

In order to obtain a *Neospora caninum* strain overexpressing GRA15, the sequence encoding GRA15II (strain Me49, sequence ToxoDB, Gene ID: 7895856, TGME49_275470) including a HA-Tag at the C-terminal end was cloned in a vector pUC8 at the Pmel site. The vector pUC8 contains 2 expression cassettes. One expression cassette encodes the chloramphenicol resistance gene in fusion with the GFP protein under the control of the pTUB5 promoter. The second expression cassette encodes the protein of interest, GRA15II, under the control of the pTUB8 promoter whose sequence includes the Kozak sequence, the translation initiation codon and the stop codon.

*Neospora caninum* NC-1 parasites ($10^7$ parasites), taken up in Cytomix medium (120 mM KCl; 5 mM $MgCl_2$; Hepes 25 mM; 10 mM $K_2HPO4/KH_2PO4$, pH 7.6; 2 mM EDTA; 0.15 mM $CaCl_2$, pH 7.6 adjusted with KOH), containing 3 mM ATP and 3 mM Glutathione were then electroporated with 50 μg of recombinant plasmid pUC8 GRA15II previously linearized with the Pcil restriction enzyme.

Then, parasites cultured on Human Foreskin Fibroblasts (HFF cells) were selected with a medium containing chloramphenicol. After eight weeks of selection, the chloramphenicol-resistant parasites were analyzed by immunoblotting to visualize the expression of the GRA15II protein.

The expression of GRA15II protein was analyzed by electrophoresis ($5.10^6$ parasites per well) followed by a transfer on nitrocellulose membrane. Briefly, parasites were suspended in sodium dodecyl sulfate-polyacrylamide gel electrophoresis (SDS-PAGE) sample buffer, sonicated, heated at 100° C. for 3 mM, and separated on a polyacrylamide gel. After electrophoresis, proteins were transferred onto a nitrocellulose membrane, which was probed with anti-HA Tag Polyclonal Antibody (71-5500—Invitrogen).

Bound antibodies were detected using anti-rabbit immunoglobulin G (IgG, whole molecule)—alkaline phosphatase conjugate (A3687—Sigma-Aldrich). Alkaline phosphatase activity was detected using the 5-bromo-4-chloro-3-indolyl phosphate/nitroblue tetrazolium (BCIP/NBT) liquid substrate system (S3771—Promega). Molecular masses standards (prestained SDS-PAGE standards, (ProSieve QuadColor Protein Markers, Lon00193837—Ozyme)) were used.

Figure 8:
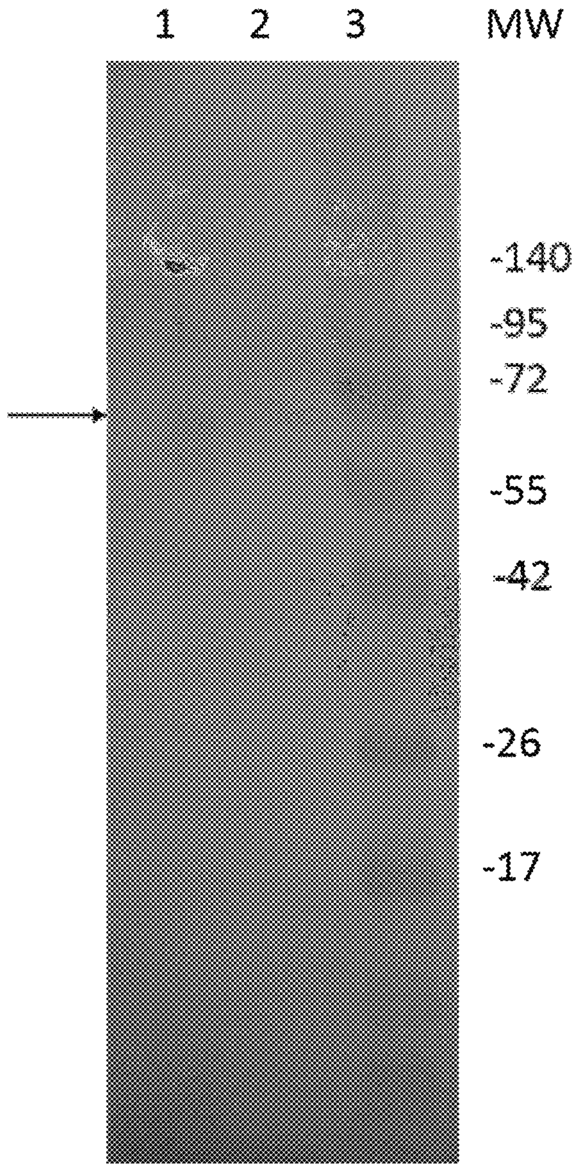
FIG. 8 is an immunoblot showing GRA15II protein expression (visualized by anti-Tag HA). The black arrow indicates the GRA15II protein expected band at 60 kDa molecular weight. Lane 1*: Neospora caninum* parasites electroporated with a plasmid encoding GRA15II. Lane 2: untransduced *Neospora caninum* parasites. Lane 3: molecular weights (MW) standards: 17, 26, 42, 55, 72, 95 and 140 kDa.

The protein is expected at 60 Kda molecular weight. A band indicated by the black arrow is visualized in Lane 1 at approximately 60 Kda (FIG. 8) showing the GRA15II protein expression in *Neospora caninum* electroporated with the PUC8 GRA15II plasmid in comparison with non-electroporated *Neospora caninum* in Lane 2 (FIG. 8) showing no band at 60 kda. Bands visualized above the indicated MW may correspond to a dimerized form of the GRA15II protein.

The invention claimed is:

1. A method for reducing a tumor size in a subject in need thereof, comprising administering to the subject a therapeutically effective amount of at least one strain of *Neospora caninum*, wherein said at least one strain of *Neospora caninum* is at a tachyzoite stage.

2. The method according to claim 1, wherein said at least one strain of *Neospora caninum* at a tachyzoite stage is a wild type strain.

3. The method according to claim 1, wherein said at least one strain of *Neospora caninum* at a tachyzoite stage is a mutant strain characterized by an over-expression of GRA15 protein, and/or by an under-expression of ROP16 protein.

4. The method according to claim 1, wherein said tumor is a solid tumor.

5. The method according to claim 1, wherein said tumor is an ovarian cancer, pancreatic cancer or melanoma.

6. The method according to claim 1, wherein said at least one strain of *Neospora caninum* at a tachyzoite stage is comprised in a composition in association with an excipient.

7. The method according to claim 1, wherein said at least one strain of *Neospora caninum* at a tachyzoite stage is comprised in a pharmaceutical composition further comprising at least one pharmaceutically acceptable excipient.

8. The method according to claim 1, wherein said at least one strain of *Neospora caninum* at a tachyzoite stage is comprised in a vaccine composition.

9. The method according to claim 1, wherein said at least one strain of *Neospora caninum* at a tachyzoite stage is comprised in a vaccine composition comprising an adjuvant.

10. The method according to claim 1, wherein said at least one strain of *Neospora caninum* at a tachyzoite stage is administered to the subject via subcutaneous, intradermal or intratumoral routes.

11. The method according to claim 1, wherein the therapeutically effective amount of *Neospora caninum* at a tachyzoite stage administered to the subject is ranging from about $10^4$ to about $10^{11}$ cells.

* * * * *